United States Patent [19]

Koszyk et al.

[11] Patent Number: 5,420,343
[45] Date of Patent: May 30, 1995

[54] DERIVATIVES OF AROMATIC CYCLIC ALKYLETHERS

[75] Inventors: Francis J. Koszyk, Prospect Heights; Richard M. Weier, Lake Bluff, both of Ill.

[73] Assignee: G. D. Searle & Co., Chicago, Ill.

[21] Appl. No.: 299,173

[22] Filed: Aug. 31, 1994

[51] Int. Cl.⁶ ............................................. C07C 59/40
[52] U.S. Cl. ..................................... 562/468; 562/431; 549/499
[58] Field of Search ................ 562/468, 431; 514/570; 549/499

[56] References Cited

U.S. PATENT DOCUMENTS

| | | | |
|---|---|---|---|
| 3,574,512 | 4/1971 | Weber et al. | 8/4 |
| 4,029,812 | 6/1977 | Wagner et al. | 424/298 |
| 4,076,841 | 2/1978 | Wagner et al. | 424/324 |
| 4,078,084 | 3/1978 | Wagner et al. | 424/324 |
| 4,153,803 | 5/1979 | Thiele et al. | 560/57 |
| 4,621,098 | 11/1986 | Umminger et al. | 514/562 |
| 4,711,903 | 12/1987 | Mueller et al. | 514/381 |
| 4,755,524 | 7/1988 | Mueller et al. | 514/381 |
| 4,801,611 | 1/1989 | Chinn et al. | 514/532 |
| 5,064,860 | 11/1991 | Mueller et al. | 514/568 |
| 5,082,854 | 1/1992 | Mueller et al. | 514/537 |
| 5,147,893 | 9/1992 | Mueller et al. | 514/530 |

FOREIGN PATENT DOCUMENTS

| | | | |
|---|---|---|---|
| 0293900 | 12/1988 | European Pat. Off. | A61K 31/19 |
| 0512559 | 11/1992 | European Pat. Off. | C07D 307/20 |
| 49116035 | of 0000 | Japan . | |
| 4-69375 | 3/1992 | Japan . | |
| WO93/10087 | 5/1993 | WIPO | C07C 323/52 |

OTHER PUBLICATIONS

Naososhima, Y. et al Agric Biol. Chem. (1984) 48(5), 1123–9.
Auer, D. E., et al. *J. Vet Pharmacol. Therap.*, 13(1):59–66 (1990).
Beiemond, P., et al. *Scand J. Rheumatology*, 19:151–156 (1990).
Caglioti, et al. "Acid Decomposition of Tosylazocyclohex-1-ene and 3-Tosylazocholesta-3, 5-diene," *J. Org. Chem.*, 38(5):920–923.
Cencetti, M., et al. *Clinincal Rheumatology*, 9(1):51–55 (1990).

(List continued on next page.)

*Primary Examiner*—Paul J. Killos
*Attorney, Agent, or Firm*—Roberta L. Hastreiter; Roger A. Williams

[57] ABSTRACT

The present invention provides compounds of the formula:

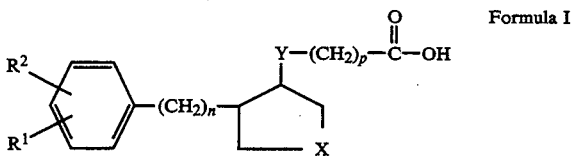

Formula I and the pharmaceutically acceptable salts thereof, wherein:
$R^1$ and $R^2$ are each alkyl;
n is an integer of from 1 to 4;
x is oxygen or $-(CH_2)_m-$;
m is an integer of from 1 to 3;
y is oxygen or sulfur; and
p is an integer of from 1 to 4.

These compounds are inhibitors of COX-I and/or COX-II, and are useful for the treatment of inflammation-associated disorders.

The present invention also provides pharmaceutical compositions comprising a therapeutically-effective amount of a compound of Formula I in combination with a pharmaceutically-acceptable carrier, and a method for treating inflammation-associated disorders in an animal comprising administering a therapeutically-effective amount of a compound of Formula I to the animal.

13 Claims, No Drawings

OTHER PUBLICATIONS

Cross, C. E., et al. *Ann. Int. Med.,* 107:526–545 (1987).

Davis, F. A., et al. "Chemistry of the Sulfur–Nitrogen Bond. VII. Rearrangement of Sulfenimines (S–Aryl Thiooximes) to Beta–Keto Sulfides. Attempted Synthesis of Benzo[b]thiophenes," *J. Org. Chem.,* 39(6): 807–809 (1974).

Kal'Yan, et al. *Izv. Akad Mauk SSSR Ser Kim,* 2:378–86 (1982).

Kanai, Kenichi CA 107:1977838.

Katayama, K., et al. *Agents and Actions,* 21(–271 (1987).

Kanofsky, J. R. *Chem. Biol. Interactions,* 70:1–28 (1989).

Katsumi, Ikuo "Studies on Styrene Derivatives," *Chem. Pharm. Bull.,* 34(4):1619–1627 (1986).

Kocan, G., et al. Inflammation Research Association, Fifth International Conference Poster Session, Abstract 20, Sep. 23–27, 1990.

Kreutner, W., et al. *J. Pharmacol. Exp. Ther.,* 247(3):997–1003 (1988).

Kukreja, R., et al. *Circulation Research,* 59 (6):612–619 (1986).

MacKenzie, N. E., et al. "Ring Contractions of Thiochroman-4-ones and Thiochromen-4-ones," *J. Chem. Soc. Perkin Trans.* 1(2):395–402.

Medvedev, A., et al. *Khimiya i Khimicheskaya Tekhnologiya,* 20 pp. 568–675 (1977).

Magerramov, et al. "Reactions to Arenesulfenyl Chlorides with Methylenecycloalkanes and Vinylcyclopropane," *Zh. Organ. Khim,* 26(11): 2333–41 (1990).

Mukaiyama, T., et al. "Reactions of Mercuric Salts with Bis(diethylthiocarbamoyl) Disulfide and Benzenesulfenyl Chloride," *J. Org. Chem.* 33(6): 2242–5 (1968).

Pushkin, et al. "Doping Effect and Acid Catalysis in the Addition of Sulfenyl Chlorides to Cyclohexene in Acetic Acid," *Zh. Organ. Khim.,* 27:(7):1473–8 (1991).

Shepherd, V. L. *Semin. Respir. Infect.* (United States) Jun., 1986, 1(2), pp. 99–106.

Trost, B. M., et al. "Hydroxysulfenylation of Olefins. An Olefin Cleavage with Functional Group Differentiation," *Journal of the American Chemical Society,* 100(22):7103–7106, Oct. 25, 1978.

Ward, P. A., et al. *Free Radical Biology & Medicine,* 5:403–408 (1988).

Youn, J. H., et al. "Synthesis of Enantiomerically Enriched α-Sulfenylated Keytones and Aldehydes," *Synthesis-Journal of Synthetic Organic Chemistry,* (2):159–161, Feb., 1987.

Zefirov, et al. "A New Method of Increasing the Effective Electrophilicity of Weak Electrophiles", p. 223.

Zefirov, N. S., et al. "Stereochemical Studies–XX Conformations of 1,2-Trans-Disubstituted Cyclohexanes," *Tetrahedron,* 32:1211–1219 (1976).

Chemical Abstracts, vol. 77, No. 7, Abstract 61306R, Aug. 14, 1972.

DERIVATIVES OF AROMATIC CYCLIC ALKYLETHERS

BACKGROUND OF THE INVENTION

1. Field of the Invention

The present invention relates to aromatic cyclic alkylethers. More particularly, the present invention relates to the novel compounds of Formula I, which inhibit cyclooxygenase I and/or II, to pharmaceutical compositions containing one or more of these compounds in combination with a pharmaceutically-acceptable carrier, and to medical methods of treatment employing these compounds.

2. Background Information

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs), and the leukotrienes, all of which have potent physiological effects.

Those compounds of the present invention which inhibit cyclooxygenase I and/or II inhibit the synthesis of prostaglandins via the cyclooxygenase pathway of arachidonic acid metabolism. These prostaglandin synthetase inhibitors may exhibit anti-inflammatory, antipyretic and analgesic activity, and are useful in the treatment of inflammatory conditions such as arthritis.

Prostaglandins play a major role in the inflammation process and the inhibition of prostaglandin production, especially production of $PGG_2$, $PGH_2$ and $PGE_2$, and have been a common target of anti-inflammatory drug discovery. However, common nonsteroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDS have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, PROC. NATL. ACAD. SCI. USA, 89, 7384 (1992), which is incorporated herein by reference, and named cyclooxygenase II (COX II) or prostaglandin G. H. synthase II. The discovery of an inducible enzyme associated with inflammation provides a viable target of inhibition which more effectively reduces inflammation and produces fewer and less drastic side effects. Cyclooxygenase II is inducible by cytokines or endotoxins, and such induction is inhibited by glucocortoids (J. Masferrer, et al, PROC. NATL. ACAD. SCI. USA, 89, 8917 (1992), which is incorporated herein by reference). The 6-methoxy-2-napthylacetic acid metabolite of nabumetone has been found by E. Meade et al. to selectively inhibit the COX II enzyme (J. BIOL. CHEM., 268, 6610 (1993), which is incorporated herein by reference). In addition, Futaki et al (GEN. PHARMAC., 24, 105 (1993), which is incorporated herein by reference,) has reported that N-(2-cyclohexyloxy-4-nitrophenyl)-methanesulfonamide is anti-inflammatory and lacks gastric side effects.

Compounds of the present invention relieve the effects of inflammation and may inhibit cyclooxygenase I and/or cyclooxygenase II.

Prior to the recognition of the significance of the arachidonic acid metabolism pathway in allergic reactions and inflammation, the search for effective therapeutic agents was based primarily on those agents which treated the symptoms of allergy and inflammation. There has since been an effort to develop new drugs which selectively block the formation of the mediators of these conditions, and the present invention provides new chemical entities which are inhibitors of the arachidonic acid pathway and are useful in the treatment of asthma, rheumatoid arthritis, osteoarthritis, psoriasis, and other allergic, hypersensitivity, and inflammatory conditions. Further examples of inflammatory conditions or diseases with an inflammatory or immune system component are disclosed in, for example, the Merck Manual of Diagnosis and Therapy, 15th Edition (1987) which is incorporated herein by reference.

Various thioether compounds have been described previously. For example, U.S. Pat. No. 4,711,903 and its continuation-in-part, U.S. Pat. No. 4,755,524, disclose compounds of the formula:

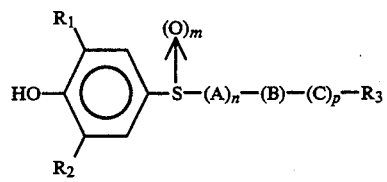

wherein: $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3; and the pharmaceutically acceptable salts thereof. The compounds are specific inhibitors of 5-lipoxygenase, and are useful in the treatment of local and systematic inflammation, allergy and hypersensitivity reactions and other disorders in which agents formed in the 5-lipoxygenase metabolic pathway are involved.

U.S. Pat. No. 4,621,098 and its equivalent, European Patent Application Publication No. 0131221, disclose compounds of the formula:

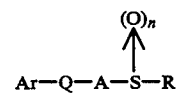

in which Ar is phenyl or phenyl substituted by one to three of varied substituents, for example, alkyl, alkoxy, hydroxy, etc.; Q is oxygen, sulfur or an NH group; A is straight or branched chain, optionally substituted, alkylene, and R is hydrogen or straight or branched alkyl, optionally substituted by alkoxy, hydroxyl, carboxyl, alkoxycarbonyl, etc.; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0, without mention of any preference among the numerous possible substituents for R or substituted phenyl as Ar.

U.S. Patent Nos. 4,029,812, 4,076,841 and 4,078,084 disclose compounds of the formula:

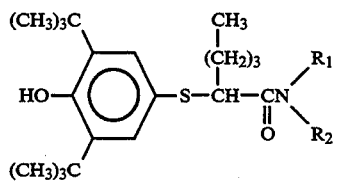

comprising 2-(3,5-di-tert-butyl-4-hydroxy-phenyl) thio carboxamides. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tert-butyl-4-hydroxythiophenol, and hydrogen sulfide to acrylate derivatives have been described. See Medvedev et al., Khimiya; Khimicheskaya Tekhnologiya, Volume 20, (1977), pp. 568-574. The compounds resulting from the foregoing process have the general formulas $RS(CH_2)_nX$ and $S(CH_2CH_3X)_2$ in which R is 3,5-di-tert-butyl-4-hydroxyphenyl and X represents, for example, $-C\equiv N$, $NH_2$, $CH(OH)CH_2Cl$, OH, COCl and various carboxy, carboxylate and amide functions.

U.S. Pat. No. 4,153,803 discloses cholesterol-lowering phenoxyalkanoic acid esters of the formula:

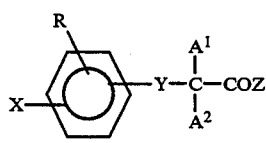

wherein, when Y is sulfur, X is hydrogen, benzyl, benzyloxy or benzylthio or substituted derivatives thereof; R is hydrogen, halogen, hydroxy, alkyl or alkoxy, $A^1$ and $A^2$ are hydrogen or alkyl and Z is amine or azacyclohydrocarbonyloxy.

JP 49116035 discloses a process for making compounds of the formula:

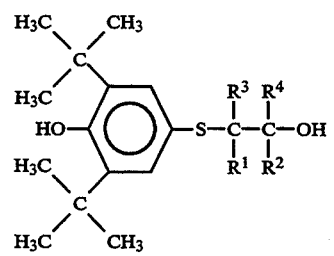

wherein $R^1$, $R2$, $R^3$ and $R^4$ are hydrogen, alkyl or aryl groups, and $R^1$ and $R^2$ can be combined to form a cycloalkyl group. The compounds are said to be useful as drug intermediates, agricultural chemicals, antioxidants and industrial chemicals. Specifically disclosed is a compound of the formula:

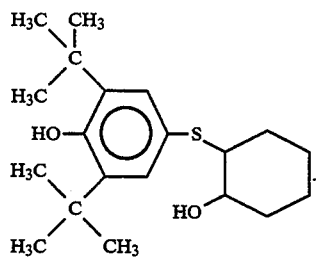

CA 107:197783q discloses dialkylphenol derivatives of the formula:

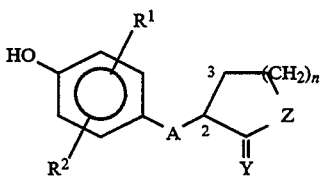

wherein $R^1$ $R^2$=alkyl; A=alkylene, S, SO; Y=alkoxyimino, O; Z=alkylene, O; n=1, 2; 2-3 saturated or unsaturated. The compounds are said to be useful as modifiers for biosynthesis of prostaglandins and leukotrienes and hypolipemics (no data).

EP0293900 discloses 5-lipoxygenase inhibiting compounds of the formula:

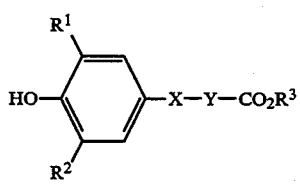

where $R^3$ and Y together are:

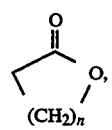

and n is 2 or 3.

Katsumi, et al., *CHEM. PHARM. BULL.* 34(4):1619-1627(1986) discloses 3,5-di-tert-butyl-4hydroxystyrenes. Some of the compounds disclosed had anti-inflammatory activity and some inhibited 5-lipoxygenase. Only one compound (Compound 3, Table I) had S attached to the 3,5-di-tert-butyl-4-hydroxyphenol. It has the following structure:

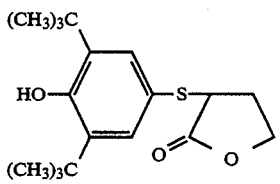

U.S. Pat. No. 4,801,611 discloses 5-lipoxygenase inhibitors of the formula:

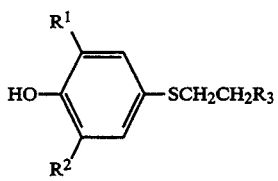

where $R_1$ and $R_2$ are tert-alkyl and $R_3$ can be:

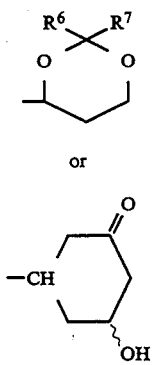

where $R_6$ and $R_7$ are $C_{1-4}$ alkyl.

Each of the documents described hereinabove discloses compounds which are structurally different from the compounds of the present invention. Thus, the compounds of the present invention are structurally distinct from that which has been described in the art.

Compounds of the present invention inhibit cyclooxygenase I and/or cyclooxygenase II, and relieve the effects of inflammation. These compounds, in addition, produce a reduced amount of side effects.

SUMMARY OF THE INVENTION

The present invention provides novel aromatic cyclic alkylethers, pharmaceutical compositions containing them and methods of using them, as well as intermediates for producing them.

The novel aromatic cyclic alkylethers of the present invention are compounds having a structure of the formula:

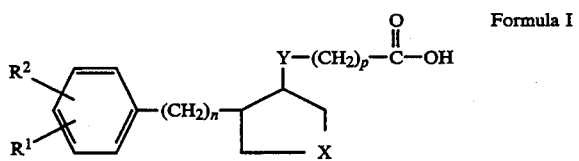

Formula I and the pharmaceutically acceptable salts thereof, wherein:

$R^1$ and $R^2$ are each alkyl;
n is an integer of from 1 to 4;
x is oxygen or —$(CH_2)_m$—;
m is an integer of from 1 to 3;
Y is oxygen or sulfur; and
p is an integer of from 1 to 4.

DETAILED DESCRIPTION OF THE PREFERRED EMBODIMENTS

1. Description of Invention

In one aspect, the present invention provides compounds comprising a structure of Formula I, as described above, and pharmaceutically-acceptable salts thereof.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

The compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts, "J. PHARM. SCI., 66, 1–19 (977), which is incorporated herein by reference.)

In another aspect, the present invention provides pharmaceutically-acceptable compositions which comprise a therapeutically-effective amount of one or more of the compounds of Formula I, as described herein, formulated together with one or more pharmaceutically-acceptable carriers. The pharmaceutical compositions of the invention may be specially formulated for oral administration in solid or liquid form, or in the form of an aerosol for inhalation, for parenteral injection, or for rectal or vaginal administration.

The present invention also comprises a method of treating inflammation or inflammation-associated disorders in an animal, the method comprising administering to the animal having such inflammation or disorder a therapeutically-effective amount of a compound of Formula I.

The most preferred embodiment of the invention is the compound described in Example 7 below.

Certain compounds of this invention may exist in geometric or stereoisomeric forms. The present invention contemplates all such compounds, including cis- and trans- geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

2. Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The term "alkyl" as used herein defines straight or branched chain monovalent hydrocarbon radicals having between about 1 to about 10 carbon atoms, within which includes from about 1 to about 6 carbon atoms, and further within which includes from about 1 to about 3 carbon atoms. Representative alkyl radicals include, for example, methyl, ethyl, propyl, isopropyl, butyl, -butyl, sec-butyl, isobutyl, pentyl, 1-methylbutyl, isopentyl, neopentyl, hexyl, octyl, nonyl, decyl, t-pentyl, etc.

The term "animal" as used herein includes mammals and nonmammals, and further includes humans and nonhuman mammals.

The term "aryl" as used herein means 5- and 6-membered single-ring aromatic radicals which may include from zero to four heteroatoms, and within which includes from zero to two heteroatoms, and further within which includes from zero to one heteroatom. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The abbreviation "b.p." as used herein means boiling point.

The term "composition" as used herein means a product which results from the combining of more than one element or ingredient.

The abbreviation "DMF" as used herein means dimethylformamide.

The abbreviation "DSC" as used herein means Differential Scanning Calorimetry.

The term "halogen" refers to chlorine, bromine, fluorine, and iodine.

The term "heteroatom" as used herein means an atom of any element other than carbon or hydrogen.

The abbreviation "HOAc" as used herein means acetic acid.

The abbreviation "HPLC" as used herein means High Pressure Liquid Chromatography.

The term "hydroxy" as used herein means the group —OH.

The abbreviation "NMR" as used herein means Nuclear Magnetic Resonance.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laureate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The expression "pharmaceutically acceptable salts" is intended to include those salts capable of being formed with the compounds of the present invention without materially altering the covalent chemical structure thereof. Such salts include inorganic and organic base or acid addition salts, such as sodium, potassium, calcium, ammonium, alkylammonium, quaternary ammonium, triethanolamine, lysine, hydrochloride, hydrobromide, phosphate, citrate, etc. well known to those skilled in the art. The foregoing salts are prepared in the conventional manner by neutralization of the compounds of formula I with the desired base or acid.

The abbreviation "t-Bu" as used herein means tert-butyl.

The abbreviation "TLC" as used herein means Thin Layer Chromatography.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

3. Utility

The compounds of Formula I are useful, for example, as anti-inflammatory and/or anti-allergy agents and in the treatment of hypersensitivity reactions, psoriasis, asthma, and related disorders and conditions in which physiologically active agents formed in the arachidonic acid metabolic pathway are involved. Compounds of the present invention may be useful in treating inflammatory and allergic conditions such as arthritis, asthma, and psoriasis.

Those compounds of the present invention which inhibit cyclooxygenase I and/or II inhibit the synthesis of prostaglandins via the cyclooxygenase pathway of arachidonic acid metabolism. These prostaglandin synthetase inhibitors may exhibit anti-inflammatory, antipyretic and analgesic activity, and are useful in the treatment of inflammatory conditions such as arthritis.

Compounds of the present invention inhibit cyclooxygenase I and/or cyclooxygenase II, and relieve the effects of inflammation. These compounds, in addition, produce a reduced amount of side effects.

Compounds of the present invention would be useful for the treatment of inflammation in an animal, and for treatment of other inflammation-associated disorders, such as an analgesic in the treatment of pain and headaches, or as an antipyretic for the treatment of fever. For example, compounds of the present invention would be useful to treat arthritis, including but not limited to rheumatoid arthritis, spondyloarthopathies, gouty arthritis, systemic lupus erythematosus, osteoarthritis and juvenile arthritis. Such compounds would be useful in the treatment of asthma, bronchitis, menstrual cramps, tendinitis, bursitis, and skin related conditions such as psoriasis, eczema, burns and dermatitis. Compounds of the present invention also would be useful to treat gastrointestinal conditions such as inflammatory bowel syndrome, Crohn's disease, gastritis, irritable bowel syndrome and ulcerative colitis. Compounds of the present invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. Compounds of the present invention are useful as anti-inflammatory agents, such as for the treatment of arthritis, with the additional benefit of having significantly less harmful side effects.

4. Dosage and Mode of Administration

The compounds of the present invention can be administered to a patient in such oral dosage forms as tablets, capsules, pills, powders, granules, elixirs, or syrups as well as aerosols for inhalation. Likewise, administration may be effected intravascularly, subcutaneously, topically, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient, the severity of the condition to be ameliorated, and the route of administration. A physician of ordinary skill can readily determine and prescribe the effective amount of the drug required to prevent, treat or arrest the progress of the condition.

Dosages of the compounds of the present invention, will range generally between 0.1 mg/kg/day to about 100 mg/kg/day, and preferably between about 0.5 mg/kg of body weight per day to about 50 mg/kg of body weight per day, when administered to patients suffering from inflammation or allergic or hypersensitivity reactions. In general, a unit dose form of the compounds of the invention will contain from about 1.75 to about 750 mg of compound. The compound may be administered in divided dosages, e.g. two or more times daily. The compounds may also be administered transdermally or topically to treat proliferative skin conditions such as psoriasis. The daily dosage may be administered in a single dose or in equal divided doses three or four times daily.

Unit dosage forms such as tablets and capsules can contain any suitable, predetermined, therapeutically effective amount of one or more active agent and a pharmaceutically acceptable carrier or diluent. Generally speaking, solid oral unit dosage forms and other unit dosage forms of the compounds of this invention will contain from 1.75 to 750 mg per tablet of drug as the effective cyclooxygenase inhibiting amount of the compound.

In the case of acute allergic or hypersensitivity reactions, it is generally preferable to administer the initial dosage via the parenteral route and continue parenteral administration until the patient is stabilized, and can be maintained, if necessary, on oral dosing.

In the case of psoriasis and other skin conditions, it may be preferred to apply a topical preparation of a compound of this invention to the affected area three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic basis.

A typical tablet of this invention can have the following compositions:

| Ingredient | Mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

In the pharmaceutical compositions and methods of the present invention, at least one of the active compounds of the invention, or a pharmaceutically acceptable salt thereof, will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like. For oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

5. Methods of Preparation

In general, the compounds of the present invention may be prepared by the methods illustrated in the following general reaction schemes, or by modifications thereof, from readily available starting materials in a conventional manner. Unless otherwise specified, the various substituents of the compounds are defined in the same manner as they are defined hereinabove in Formula I.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The compounds of the present invention may be synthesized by the procedures described in General Reaction Scheme 1 presented herein. Alkylation of beta-ketoesters 1 is accomplished by treatment with a base followed by reaction of the resultant anion with an aralkyl halide or sulfonate ester 2. The bases used include, but are not limited to, sodium hydride, lithium hydride, potassium hydride, lithium bis(trimethylsilyl)amide, sodium amide, potassium t-butoxide, and the like, in an inert solvent such as benzene, toluene, dimethylformamide, tetrahydrofuran, diethyl ether, dioxane, and the like, or the conjugate bases of acidic solvents such as, e.g., sodium methoxide in methanol, sodium ethoxide in ethanol, or the sodium salt of dimethylsulfoxide in dimethylsulfoxide, and the like. The aralkyl halides can include chlorides, bromides, or iodides, either preformed or formed in situ as occurs with chlorides or tosylates in the presence of sodium iodide. Sulfonate esters can include p-toluenesulfonates, methanesulfonates, p-bromobenzenesulfonates, trifluoromethanesulfonates, and the like.

Decarbalkoxylation of the derived alkylated beta-keto esters to give ketones 3 is accomplished by acidic hydrolysis of the ester using mineral acids, such as hydrochloric acid or hydrobromic acid, in a solvent such as acetic acid, followed by thermolytic decarboxylation, either in a one pot procedure or by separate decarboxylation of the isolated beta-keto acid. Alternatively, the decarbalkoxylation can be accomplished by reaction of the beta keto ester with e.g. lithium iodide or alkali metal thiolates such as sodium thiomethoxide or lithium thiopropoxide in dimethylformamide. The resulting ketones 3 may be reduced to the corresponding cis and trans alcohols 4 using a suitable reducing agent. Such agents include, but are not limited to, sodium borohydride, lithium aluminum hydride and its alkoxylated derivatives, and diisobutylaluminum hydride. In addition, reduction can be accomplished with hydrogen gas in the presence of a metal catalyst such as platinum or rhodium, either as the zero valent metals, free or supported on a carrier such as carbon, or in the form of a complex, either achiral or chiral and nonracemic.

The cis and trans alcohols 4 may be alkylated to give the compounds of the present invention directly by using halocarboxylic acids or sulfonyloxycarboxylic acids in the presence of a suitable base in an appropriate solvent to give the corresponding 5-cis and 5-trans acids. The bases used include, but are not limited to, sodium hydride, lithium hydride, potassium hydride, lithium bis(trimethylsilyl)amide, sodium amide, potassium t-butoxide, and the like, in an inert solvent such as benzene, toluene, dimethylformamide, N-methylpyrrolidone, dimethylacetamide, tetrahydrofuran, diethyl ether, dioxane, dimethylsulfoxide, and the like. Alternatively, the alkylating agent can be an halocarboxylic acid ester or sulfonyloxycarboxylic acid ester, in which case the product is the corresponding carboxylic acid ester. The esters can then be hydrolyzed to give the compounds of the present invention under basic or acidic conditions. Basic conditions include for example sodium hydroxide, lithium hydroperoxide, or potassium hydroxide in mixtures of water and alcohols or of water and ethers such as tetrahydrofuran or dioxane. Acidic conditions include for example acids such as hydrochloric acid or sulfuric acid in mixtures of water and alcohols or of water and ethers such as tetrahydrofuran or dioxane. Ester hydrolysis can additionally be accomplished by the use of esterases such as lipases. Enzymatic hydrolysis can be expected to provide a single chiral nonracemic carboxylic acid from a racemic mixture of esters. Compounds 7 where the linking atom is sulfur, may also be synthesized from alcohols 4-cis and 4-trans. These may be converted to sulfonate esters 6-cis and 6-trans by treatment with an appropriate alkyl or aryl sulfonyl halide or anhydride in the presence of a base. Examples of appropriate sulfonyl halides and anhydrides include p-toluenesulfonyl chloride, methanesulfonyl chloride, and trifluoromethanesulfonic anhydride. Examples of suitable bases include triethylamine, pyridine, 2,6-lutidine, and ethyldiisopropylamine. Suitable solvents for the reaction include dichloromethane, 1,2-dichloroethane, and tetrahydrofuran.

Compounds 6 may be converted to thio compounds 7 by reaction with thioalkylcarboxylic acids or their esters in the presence of a base. An example of a thioalkylcarboxylic acid ester is methyl thioglycolate. Suitable bases include potassium carbonate, triethylamine and sodium methoxide, in solvents such as dimethylformamide, tetrahydrofuran, or methanol. In the case where a carboxylic acid ester is used as the reaction partner, ester hydrolysis is then carried out as described above for the corresponding oxo compounds.

Alternatively, compounds 7 may be converted to thio compounds 7 by reaction of alcohols 4 with a mixture of triphenylphosphine and diethyl diazodicarboxylate in a solvent such as tetrahydrofuran followed by reaction with thioalkylcarboxylic acids or their esters in the same reaction vessel. Such a procedure has the advantage of avoiding a separate isolation step.

Alternatively compounds 7 may be synthesized from sulfonate esters 6 by conversion to thiols 8-cis and 8-trans by first reaction with a suitable protected sulfur nucleophile and then deprotection to the thiol. Suitable sulfur nucleophiles include potassium thioacetate, thiourea, and potassium thiocyanate. Deprotection can be effected by treatment with a base, e.g. sodium hydroxide in mixtures of water and alcohols. Thiols 8 may be converted to compounds 7 by reaction as described above for the corresponding oxo compounds.

using HPLC. The enantiomerically pure alcohol (Enantiomer A) may be separated from enantiomerically pure acetate by column chromatography. Saponification of

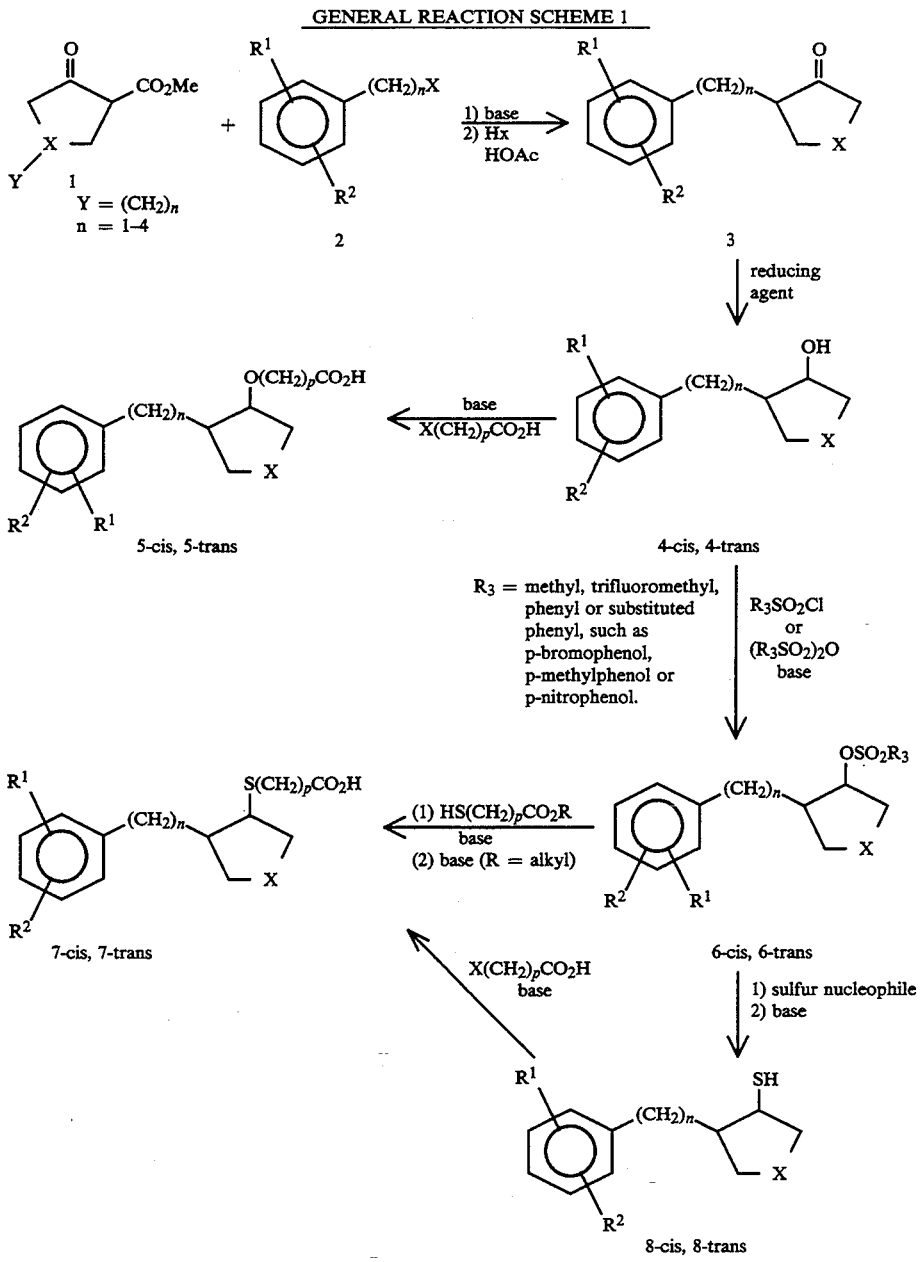

GENERAL REACTION SCHEME 1

In addition, enzymatic resolution of a suitable synthetic intermediate may be carried out. Thus, racemic alcohols 4-cis and 4-trans may be resolved to their respective single enantiomers by the procedure illustrated in General Reaction Scheme 2. Treatment of either the racemic cis or racemic trans alcohol with an acetylating agent, such as vinyl acetate or isopropenyl acetate, in the presence of an appropriate enzyme, such as AMANO Lipase PS30, results in the selective acetylation of one of the constituent enantiomeric alcohols, leading to a crude product consisting of essentially enantiomerically pure acetate and essentially enantiomerically pure alcohol (Enantiomer A). Appropriate enzymes include, but are not limited to, lipases, cholinesterases and proteases. The reaction may be monitored to complete acetylation of one of the enantiomers the acetate using aqueous base provides the other enantiomerically pure alcohol (Enantiomer B). Conversion of these alcohols to enantiomerically pure acids (5, General Reaction Scheme 1) is effected by treatment with a haloalkyl carboxylic acid or its salt, such as sodium chloroacetate, in the presence of a base, as is shown in General Reaction Scheme 1.

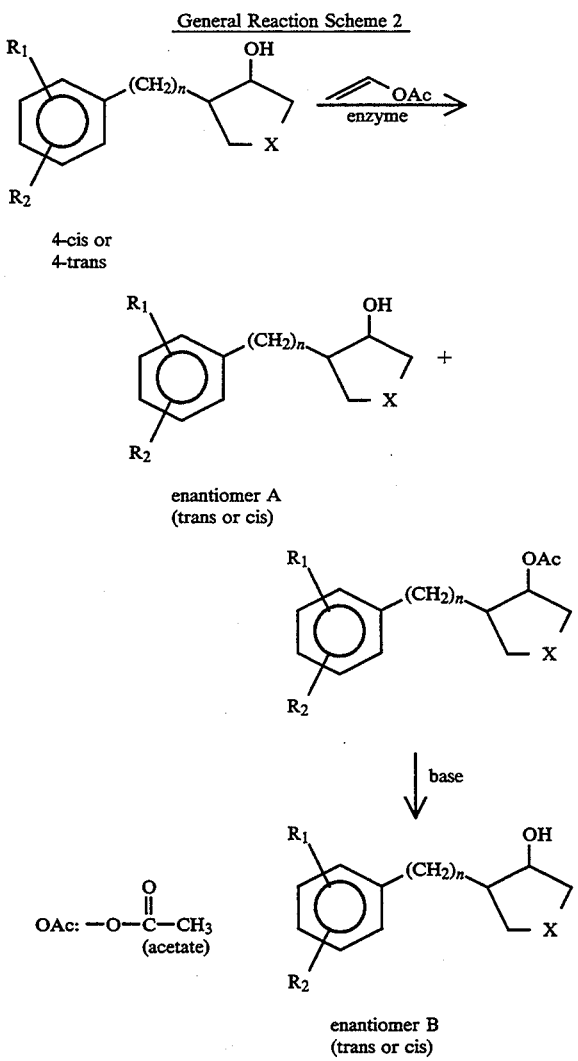

The conditions for carrying out the individual steps in each of the general reaction schemes presented above are conventional, well-known, and capable of wide variation.

Other methods known in the art can also be used to synthesize the compounds of the present invention.

6. Biological Evaluations

The compounds of the invention are evaluated with respect to COX-I and COX-II activity in vitro using an enzyme based assay according to the following assay procedure.

Commercially available nonsteroidal anti-inflammatory drugs are believed to work through the inhibition of COX-I and COX-II activity in vivo to block local proinflammatory prostaglandin production, often at the site of tissue injury.

(a) preparation of Recombinant COX Baculoviruses

A 2.0 kb fragment containing the coding region for either human or murine COX-I (Caymen Chemical, Ann Arbor, Mich.), or human or murine COX-II (Caymen Chemical, Ann Arbor, Mich.), was cloned into a BamH1 site of the baculovirus transfer vector pVL1393 (Invitrogen, Palo Alto, Calif.) to generate a baculovirus transfer vector. Recombinant baculoviruses were isolated by transfecting 4 μg of baculovirus transfer vector DNA into SF9 cells (2×10e8) (Invitrogen, Palo Alto, Calif.) along with 200 ng of linearized bacium by the phosphate method. See M. D. Summers et al., "A Manual of Methods for Baculovirus Vectors and Insect Cell Culture Procedure," *TEXAS AGRICULTURE EXPERIMENTAL STATION BULLETIN*, No. 1555 (1987), which is incorporated herein by reference. Recombinant viruses were purified by three rounds of plaque purification, and high titer (10e7–10e8 pfu/ml) stocks of virus were prepared. For large scale production, SF9 insect cells (Invitrogen, Palo Alto, Calif.) were infected in 10 liter fermentors (0.5×10⁶/ml) with the recombinant baculovirus stock, such that the multiplicity of infection was 0.1. After 72 hours, the cells were centrifuged and the cell pellet was homogenized in Tris/Sucrose (50 mM: 25%, pH 8.0) containing 1% CHAPS. The homogenate was centrifuged at 10,000xG for 30 minutes, and the resultant supernatant was stored at −80° C. before being assayed for COX activity.

b. Assay for COX-I and COX-II activity:

COX activity was assayed as $PGE_2$ formed/μg protein/time using an ELISA (Caymen Chemical, Ann Arbor, Mich.) to detect the prostaglandin E2 released. CHAPS-solubilized insect cell membranes containing the appropriate COX enzyme were incubated in a potassium phosphate buffer (50 mM, pH 8.0) containing phenol (0.5 mM), and heme (1 μM) with the addition of arachidonic acid (10 μM). Compounds of the present invention were pre-incubated with the enzyme for 10–20 minutes prior to the addition of the COX-I and COX-II enzyme substrate arachidonic acid (10 μM). Any reaction between the arachidonic acid and the enzyme was stopped after ten minutes at 37° C./room temperature by transferring 40 μl of reaction mix into 160 μM ELISA buffer and 25 μM indomethacin. The $PGE_2$ formed was measured by standard ELISA technology (Cayman Chemical, Ann Arbor, Mich.).

The results of this assay are presented in Table 1 hereinbelow. The results for this assay, as well as for the next assay (COX-II Cell Fibroblast Assay) are expressed in terms of COX-I or II activity as an IC50 value (50% inhibitory concentration), as defined as the amount of prostaglandin $E_2$ ($PGE_2$) formed per protein per time in response to the enzyme substrate arachidonic acid.

The compounds of the invention are evaluated with respect to the inhibition of cellular COX-II in vitro according to the following Cellular COX-II Assay (Cell Fibroblast Assay).

Cellular COX-II Assay (Cell Fibroblast Assay)

Inhibition of cellular COX-II by test compounds is determined using stimulated human fetal dermal fibroblasts (HFDF, derived from primary cell cultures). Fibroblasts are cultured in microtiter wells at 1.5×10⁴ cells/well in Dulbecco's Modified Eagle's Media (DMEM)(Gibco/BRL, Gaithersburg, Md.; Sigma Chemical Co., St. Louis, Mo.) containing 4500 mg glucose/L, 100 units penicillin G/ml and 0.1 mg streptomycin/ml, 4 mM L-glutamine, 25 mM Hepes and 10% Fetal Bovine Serum (Gibco/BRL, Gaithersburg, Md.; Bioproducts For Science, Inc., Indianapolis, Ind.). Following a 3-day incubation at 37° C., the culture media is removed by aspiration using low vacuum, and the cells are stimulated overnight with medium containing human recombinant IL-1 (interleukin-1) beta (1 ng/ml)(Cistron, Pine Brook, N.J.). The next day, the fibroblasts are washed with Phosphate Buffered Saline, and 185 μl of DMEM is added to each well. The cells are placed in a 37° C. incubator for 15 minutes. Compounds are then added to the cells using seven half-log dilutions in duplicate determinations. Cells are incubated with test compounds at 37° C. for 30 minutes. The COX-II substrate arachidonic acid (20 μM; Nu-Chek-Prep Inc., Elysian, Minn.) is then added to the cell cultures and the plates are incubated for 10 minutes at 37° C. Supernatants are collected and Prostaglandin $E_2$ ($PGE_2$) production is measured by an enzyme-linked immunosorbent assay (ELISA; antibodies produced by Cayman Chemical Company, Ann Arbor, Mich.). Compounds which exhibit activity in this assay inhibit $PGE_2$ production.

The following is a description of how the activities of the compounds of the present invention may be determined.

A run of this assay consists of one (or more) plates, each containing, along with the standard (in row A), (1) two wells of unstimulated material (in col. 12), (2) five wells of stimulated material (in col. 12), (3) seven wells (one per concentration) for indomethacin (in col. 11), and (4) two wells at each of seven concentrations for five test compounds, one of which is a repeat of indomethacin. The response (ng/ml Eicosanoid) is estimated from the Standard curve and is highest at low concentrations and decreases as the concentration increases. If the response is plotted on the y-axis and the log of the concentration is plotted on the x-axis, the dose-response pattern for these assays is typically a symmetrical, sigmoidal shaped curve. If a full range of concentrations is used, the complete sigmoidal curve may be seen, starting with an upper asymptote, falling at some degree of steepness, and then leveling off at a lower asymptote. The IC50 is defined as the concentration corresponding to a response midway between the upper and lower plateaus. A theoretic "dose-response" model is used to estimate the $IC_{50}$.

The procedure described below was used to define the minimum and maximum responses for the compounds on a plate.

The procedure uses information for indomethacin and the rest of the plate in defining the minimum and maximum response. The justification for doing this is as follows. Enough runs have been done with indomethacin to determine and use a range of concentrations such that the response to the lowest concentrations is on the upper plateau of the sigmoidal curve and the response to the highest concentrations is on the lower plateau of the sigmoidal curve. For the other compounds, if a response is measured which is less than the response for the unstimulated wells, then this response may be considered to be another estimate of a minimal response. Likewise, if a response is measured which is greater than the response for the stimulated wells, then this response may be considered to be another estimate of a maximal response.

Based on this reasoning, the minimum is estimated as follows:

1) For each compound, including indomethacin (col. 11), identify the smallest dup average,
2) If the compound is indomethacin (col. 11), mark this response for use,
3) If the compound is not indomethacin and the response is less than the average of the unstimulated wells, mark this response for use,
4) Calculate the minimal response as the average of the unstimulated wells along with the dup averages marked for use in steps 2 and 3 above.

Likewise, the maximum is estimated as follows:

1) For each compound, including indomethacin (col. 11), identify the largest dup average,
2) If this largest dup average does not correspond to the lowest concentration, compute the mean of the dup averages for this concentration and all lower concentrations,
3) If the compound is indomethacin (col. 11), mark this response (or mean) for use,
4) If the compound is not indomethacin and the response (or mean) is greater than the average of the stimulated wells, mark this response for use,
5) Calculate the maximal response as the average of the stimulated wells along with the responses (or means) marked for use in steps 3 and 4 above.

Then, the model used to estimate the ICs0 is the four parameter logistic with two parameters fixed, the minimum and maximum. This mode is described in A. De Lean et al. "Simultaneous analysis of families of sigmoidal curves: application to bioassay, radioligand assay, and physiological dose-response curves", *AM. J. PHYSIOL.* 235(2): E97–E102, (1978), which is incorporated herein by reference. The formula for the four-parameter logistic model may be expressed as:

$$Y = ((a-d)/(1+(X/c)**b) + d,$$

where Y is the response, X is the concentration, a is the lower asymptote, d is the upper asymptote, c is the $IC_{50}$ (in the same units as X), b is the slope and ** means exponent. For this assay, a is fixed at the minimum value and d is fixed at the maximum value as calculated above.

A nonlinear modeling procedure is used to estimate the two other parameters, the slope and $IC_{50}$. Nonlinear modeling requires the specification of starting values for each parameter to be estimated, and then, unlike linear modeling, an iterative procedure is required to improve on these initial estimates until no further improvement in the fit of the model to the observed data can be achieved (or the maximum number of iterations has been reached). The criteria for a good fit is least squares, i.e., the best fit is one for which the sum of the distance squared between each observed data point and the model at that same concentration is minimized (is least).

Two follow-up measures are provided to insure that the final solution is adequate. First, a plot of the observed data with the estimated model curve superimposed is created. Second, the value of the RMSEs (root mean squared errors) generated for each model fit by this assay is printed. A simplified description of the RMSE is that it is the average distance of the observed data from the model, in terms of counts per minute. (The RMSE is actually the square root of the sum of the distance squared between each observed data point and the model as determined by the final solution divided by the number of concentration levels minus 2.) Smaller values of RMSE indicate closer fits of the model to the observed data. Unusually large values of RMSE should be investigated.

For further details concerning this Cellular COX-II Assay (Cell Fibroblast Assay), see A. Raz et al., "Temporal and Pharmacological Division of Fibroblast Cyclooxygenase Expression into Transcriptional and Translational Phases," *PROC. NATL. ACAD. SCI., U.S.A.,* 86:1657–1661 (1989), which is incorporated herein by reference.

The results with respect to the title compound of Example 8 shown and described hereinbelow for the above-described assay is also set forth in Table 1 below.

TABLE 1

| Compound Example Number | Human Enzyme Assay IC$_{50}$ (μM) | | Cell Fibroblast Assay IC$_{50}$ (nM) |
| --- | --- | --- | --- |
| | COX-II | COX-I | |
| 8 | >100 | >100 | 2.0 |
| 7 | 1.339 | >100 | Not Tested |

7. Examples

The following non-limiting examples further describe and illustrate details for the preparation of the compounds of the present invention. Those skilled in the art will readily understand and appreciate that known variations of the conditions and procedures in the following preparative methods can be utilized.

In these examples, all temperatures are degrees Celsius unless otherwise noted. Melting points were determined on a Fisher-Johns melting point apparatus or by DSC and are uncorrected.

Unless indicated otherwise in a particular example, all of the starting materials, and all of the equipment, employed in the examples are commercially available. Sources for these materials include Sigma Chemical Co. (St. Louis, Mo.), Aldrich Chemical Co. (Milwaukee, Wis.), Lancaster Synthesis (Windham, N.H.), Bioproducts For Science, Inc. (Indianapolis, Ind.), Fisher Scientific (Pittsburgh, Pa.), Boehringer Mannheim Biochemicals (Indianapolis, Ind.), Fluka Chemical Corp. (Ronkonkoma, N.Y.), TCI, American Tokyo Kasei, Inc. (Atlanta, Ga.), Chemical Dynamics Corp. (South Plainfield, N.J.), Amano International Enzyme Company, Inc. (Troy, Va.), Nu-Chek-Prep, Inc. (Elysian, Minn.), Cayman Chemical (Ann Arbor, Mich.), Cistron (Pine Brook, N.J.), Gibco/BRL (Gaithersburg, Md.) and Invitrogen (Palo Alto, Calif.). Most of the starting materials were obtained from Aldrich Chemical Co. (Milwaukee, Wis.). The syntheses of those starting materials which are not commercially available are described in the examples presented below.

All patents and publications referred to in the examples, and throughout the specification, are hereby incorporated herein by reference, without admission that such is prior art.

EXAMPLE 1

Methyl 3,5-bis(1,1-dimethylethyl)benzoate (1)

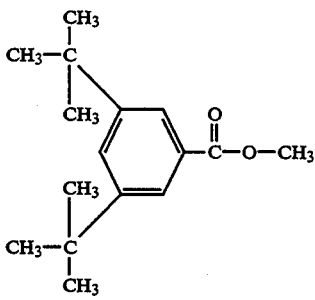

To a solution of 5.50 g (23.5 mmoles) of 3,5-di-t-butylbenzoic acid in 25 ml of dry dimethylformamide was added 5.01 g (35.3 mmoles) of iodomethane, and then 6.49 g of anhydrous potassium carbonate. After stirring at room temperature for 2 hours, water was added, the mixture was extracted three times with diethyl ether, the combined organic extracts were washed with brine, dried over sodium sulfate, filtered, and evaporated to give 5.68 g of the title compound as a crystalline solid, m.p. 52.0°-52.5° C. The structural assignment was supported by $^1$H NMR.

EXAMPLE 2

3,5-bis(1,1-dimethylethyl)benzenemethanol (2)

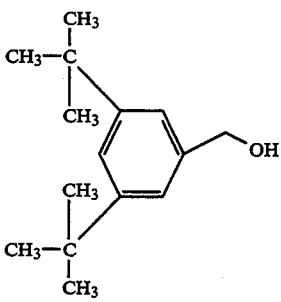

To a solution of 5.68 g (22.9 mmoles) of the title product of Example 1 in 160 ml of dry tetrahydrofuran stirring at −78° under nitrogen was added dropwise 69 ml of 1M diisobutylaluminum hydride in toluene. The mixture was allowed to warm to room temperature over 3 hours, after which methanol was added to the mixture. The resulting thick gelatinous mass was added to dilute aqueous hydrochloric acid, extracted with several portions of diethyl ether, and the combined organic extracts were washed with brine, dried over sodium sulfate, filtered, and evaporated to give the title compound (4.88 g) as a colorless oil. The structural assignment was supported by $^1$H NMR.

EXAMPLE 3

3,5,bis(1,1-dimethylethyl)chloromethylbenzene (3)

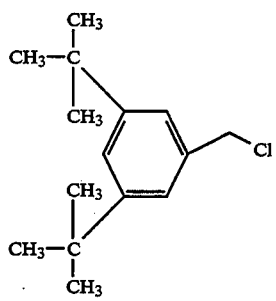

To a solution of 2.00 g (9.09 mmoles) of the title product of Example 2 and 719 mg (9.09 mmoles) of pyridine in 25 ml of dry diethyl ether was added slowly 3.3 g (27 mmoles) of thionyl chloride. During the addition, the mixture refluxed gently. After further stirring at room temperature, water was added, the resulting mixture was partitioned between diethyl ether and water, the aqueous layer was further extracted with ether, and the combined organic extracts were washed with brine, dried over sodium sulfate, filtered, and evaporated. Chromatography of the residue over silica gel using hexane as eluent gave the title compound (1.29 g) as a colorless oil. The structural assignment was supported by $^1$H NMR.

EXAMPLE 4

Methyl 1-[3,5-bis(1,1-dimethylethyl)phenyl]methyl]-2-oxocyclopentane-1-carboxylate (4)

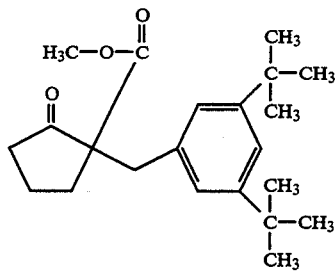

To a suspension of 259 mg of 60% sodium hydride dispersion in mineral oil in 5 ml of benzene was added dropwise a solution of 2-carbomethoxycyclopentanone in 2 ml of benzene. A further 2 ml of benzene was added to facilitate stirring. The mixture was stirred at reflux for 30 minutes, a solution of 1.29 g (5.40 mmoles) of the title product of Example 3 in 5 ml of benzene was added, and the mixture was refluxed for 8 hours. After cooling, water was added, the mixture was partitioned between diethyl ether and dilute aqueous hydrochloric acid, the aqueous layer was extracted with ether, and the combined organic extracts were washed with brine, dried over sodium sulfate, filtered, and evaporated. Chromatography of the residue over silica gel using 10% ethyl acetate/hexane as eluent gave the title compound (1.02 g) as a colorless oil. The structural assignment was supported by $^1$H NMR.

Analysis Calculated for $C_{22}H_{32}O_3$ (MW 344.50):
Calculated: C, 76.70;, H, 9.36.
Found: C, 76.44; H, 9.48.

EXAMPLE 5

2-[3,5-bis(1,1-dimethylethyl)phenylmethyl]-cyclopentanone (5)

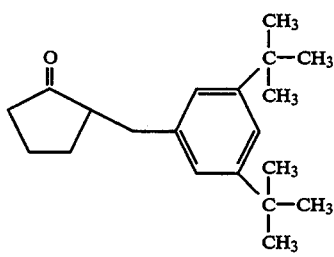

To a solution of 944 mg (2.74 mmoles) of the title product of Example 4 in 20 ml of acetic acid was added 20 ml of concentrated hydrochloric acid. The mixture was stirred at reflux for 6 hours and then cooled to room temperature. After azeotropic distillation of most of the acetic acid with toluene, water was added, the mixture was extracted with 50/50 diethyl ether-toluene, further extracted twice with toluene, and the combined organic extracts were washed with aqueous sodium bicarbonate and then brine, dried over sodium sulfate, filtered, and evaporated to give the title compound (750 mg) as a colorless oil.

Analysis Calculated for $C_{20}H_{30}O$ (MW 286.46):
Calculated: C, 83.86; H, 10.56.
Found: C, 84.07; H, 10.87.

EXAMPLE 6

(cis)-2-[3,5-bis(1,1-dimethylethyl)-phenylmethyl]cyclopentanol (6)

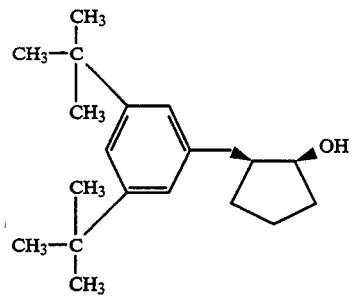

Compound A

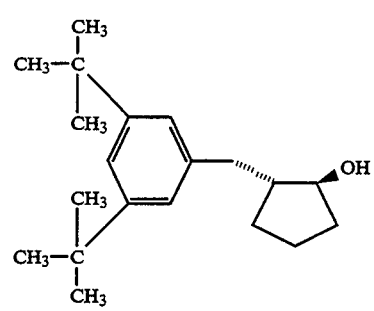

Compound B

To a solution of 710 mg (2.48 mmoles) of the title product of Example 5 in 25 ml of ethanol was added dropwise a solution of 188 mg (4.97 mmoles) of sodium borohydride in 3 ml of water. After 30 minutes, acetic acid was added, most of the ethanol was evaporated, the residue was partitioned between diethyl ether and dilute aqueous hydrochloric acid, the aqueous layer was further extracted with ether, and the combined organic extracts were washed with brine, dried over sodium sulfate, filtered, and evaporated. Chromatography of the residue using 15% ethyl acetate/hexane as eluent gave the title cis isomer (105 mg) and the title trans isomer (155 mg) as colorless oils. The structures were supported by $^1$H NMR.

EXAMPLE 7

(cis)-2-[[2-[3,5-bis(1,1-dimethylethyl)-phenylmethyl]cyclopentyl]oxy]-acetic acid (7)

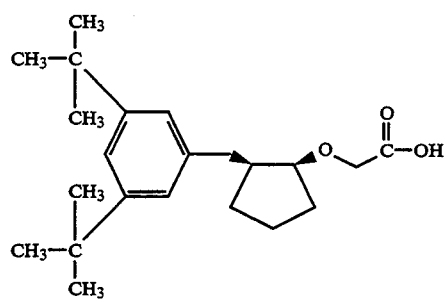

To a solution of the title cis isomer of Example 6 (103 mg, 0.358 mmole) in 3 ml of dry dimethyl sulfoxide was added 29 mg of 60% sodium hydride dispersion in mineral oil. The mixture was stirred under argon while heating to 80°. After 30 minutes, sodium chloroacetate (83 mg) was added and stirring continued for 16 hours.

After cooling, the mixture was partitioned between diethyl ether and dilute aqueous hydrochloric acid, the aqueous layer was further extracted with ether. The combined organic extracts were washed with several portions of water, and then with brine, dried over sodium sulfate, filtered, and concentrated. Chromatography of the residue over silica gel using 25% ethyl acetate/hexane then 25% ethyl acetate/2% acetic acid/73% hexane gave the title compound (29 mg) as an oil. The structural assignment was supported by the $^1$H NMR spectrum.

Analysis Calculated for $C_{22}H_{34}O_3 \cdot \frac{1}{4}$ $H_2O$ (MW 351.01):

Calculated: C, 75.28; H, 9.76.

Found: C, 75.29; H, 9.77.

EXAMPLE 8

(trans)-2-[[2-[3,5-bis(1,1-dimethylethyl)-phenylmethyl]cyclopentyl]oxy]acetic acid (8)

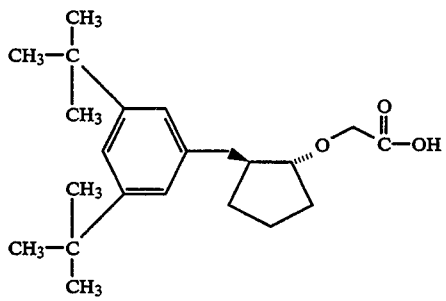

The title compound (90 mg) was prepared by the method described in Example 7, except that the title trans isomer of Example 6 was used in place of the title cis isomer of Example 7, and that the reaction was carried out for 6 hours instead of 16 hours. The structural assignment was supported by the $^1$H NMR spectrum.

Analysis Calculated for $C_{22}H_{34}O_3 \cdot \frac{1}{8}$ $H_2O$ (MW 348.76):

Calculated: C, 75.77; H, 9.83.

Found: C, 75.79; H, 9.95.

EXAMPLE 9

2,4-bis(1,1-dimethylethyl)-1-bromobenzene (9)

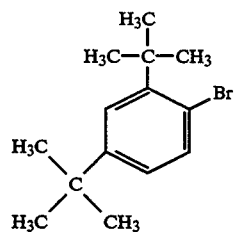

The title compound was prepared from 1,3-di-t-butylbenzene by the method described by A. T. Fry et al., "2 4-di-t-Butylbromobenzene by Silver Ion-Assisted, Bromination of 1,3-di-t-Butylbenzene," ORG. PREP. AND PROCED. INT., 23, (4), 425-427 (1991), which is incorporated herein by reference.

To a solution of 5.00 g (26.3 mmoles) of 1,3-di-t-butylbenzene in 15 ml of acetic acid was added 4.47 g (26.3 mmoles) of silver nitrate. The mixture was stirred in an oil bath at 75°-80° and then bromine (4.21 g, 26.3 mmoles) was added in small portions over 2 hours. After the addition was complete, the reaction mixture was stirred for a further 45 minutes. After cooling, the precipitated silver bromide was filtered off and washed with acetic acid. The combined filtrates were partitioned between dichloromethane and water and the aqueous layer was further extracted with dichloromethane. The combined organic extracts were washed with aqueous sodium bisulfite, dried over sodium sulfate, filtered, and evaporated. Acetic acid was then removed by azeotropic distillation with heptane. Distillation of the residue under reduced pressure gave 7.07 g of the title compound, b.p. 82°-84° C. (1 mm). The structural assignment was supported by $^1$H NMR and $^{13}$C NMR.

EXAMPLE 10

2,4-bis(1,1-dimethylethyl)benzeneethanol (10)

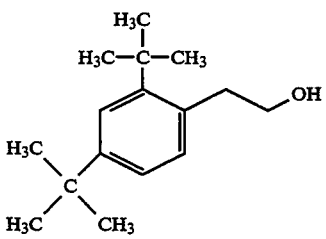

To 243 mg (10 mmoles) of magnesium turnings in 10 ml of tetrahydrofuran is added dropwise a solution of 2.69 grams (10 mmoles) of the title product of Example 9 in 5 ml of tetrahydrofuran. After the addition is complete, the mixture is refluxed for one hour. Ethylene oxide (440 mg, 10 mmoles) is then added, and refluxing continued for one hour. The mixture is cooled to room temperature and partitioned between saturated ammonium chloride and diethyl ether. The aqueous layer is further extracted with ether, the combined organic extracts washed with brine, dried over sodium sulfate, filtered, and evaporated. Chromatography of the residue over silica gel using mixtures of ethyl acetate and hexane as eluents gives the title compound.

EXAMPLE 11

2,4-bis(1,1-dimethylethyl)-1-(2-chloroethyl)benzene (11)

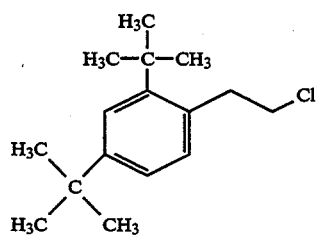

A solution of the title product of Example 10 (2.0 grams, 8.5 mmoles) and thionyl chloride (2.03 g, 17.1 mmoles) in toluene (50 ml) is heated at reflux for one hour. After cooling, the mixture is evaporated. Chromatography of the residue over silica gel using mixtures of ethyl acetate and hexane as eluents gives the title compound.

EXAMPLE 12 methyl1-[2-[2,4-bis(1,1-dimethylethyl)phenyl]ethyl]-2-oxocyclopentanecarboxylate (12)

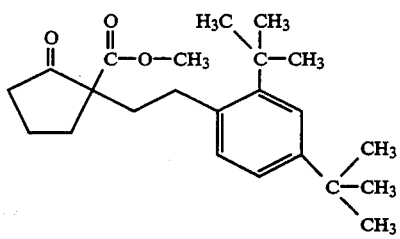

The title compound is prepared by the method of Example 4, except that the title product of Example 11 is used in place of the title product of Example 3.

EXAMPLE 13

2-[2-[2,4-bis(1,1-dimethylethyl)phenyl-ethyl]cyclopentanone (13)

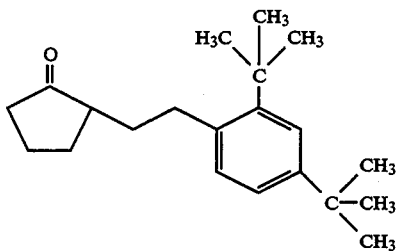

To a solution of 944 mg (2.74 mmoles) of the title product of Example 12 in 20 ml of acetic acid is added 20 ml of concentrated hydrochloric acid. The mixture is stirred at reflux for 6 hours and then cooled to room temperature. After azeotropic distillation of most of the acetic acid with toluene, water is added and the mixture is extracted first with 50/50 diethyl ether/toluene, and then further extracted twice with toluene. The combined organic extracts are washed with aqueous sodium bicarbonate and then brine, dried over sodium sulfate, filtered, and evaporated. Chromatography of the residue over silica gel using mixtures of ethyl acetate and hexane as eluents gives the title compound.

EXAMPLE 14

(cis)-2-[2-[2,4-bis(1,1-dimethylethyl)phenyl]-ethyl]cyclopentanol(14, Compound A) and (trans)-2-[2-[2,4-bis(1,1-dimethylethyl)phenyl]-ethyl]cyclopentanol (14, Compound B)

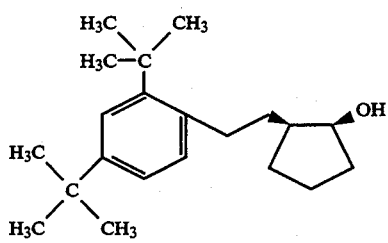

Compound A

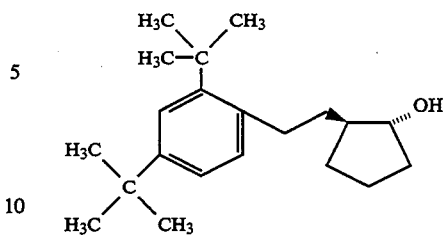

Compound B

To a solution of 710 mg (2.48 mmoles) of the title product of Example 13 in 25 ml of ethanol is added 188 mg (4.97 mmoles) of sodium borohydride. After 30 minutes, acetic acid is added, the solution concentrated, and the residue is partitioned between diethyl ether and dilute aqueous hydrochloric acid. The aqueous layer is further extracted with ether and the combined organic extracts are washed with brine, dried over sodium sulfate, filtered, and evaporated. Chromatography of the residue using mixtures of ethyl acetate and hexane as eluents gives the title cis isomer (Compound A) and the title trans isomer (Compound B).

EXAMPLE 15

(cis)-2-[[2-[2-[2,4-bis(1,1-dimethylethyl)phenyl]-ethyl]-cyclopentyl]oxy]acetic acid (15)

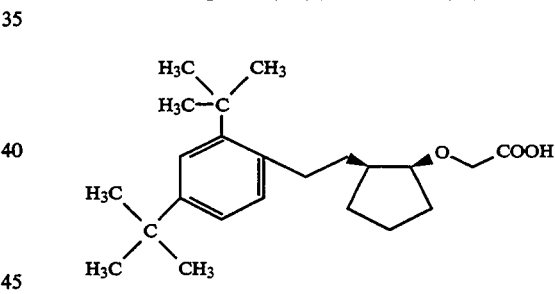

To a solution of the title cis isomer of Example 14 (103 mg, 0.358 mmole) in 5 ml of dry dimethyl sulfoxide is added 29 mg of sodium hydride dispersion (60% in mineral oil, 0.71 mmol). The mixture is stirred under argon while heating to 80°. After 30 minutes sodium chloroacetate (83 mg) is added and stirring continued for 16 hours. After cooling, the mixture is partitioned between diethyl ether and dilute aqueous hydrochloric acid. The aqueous layer is further extracted with ether, the combined organic extracts washed with several portions of water, and then with brine. The solution is dried over sodium sulfate, filtered, and concentrated. Chromatography of the residue over silica gel using mixtures of ethyl acetate and hexane, then mixtures of ethyl acetate, hexane, and acetic acid as eluents gives the title compound.

EXAMPLE 16

(trans)-2-[[2-[2-[2,4-bis(1,1-dimethylethyl)phenyl]-ethyl]cyclopentyl]Oxy]acetic acid (16)

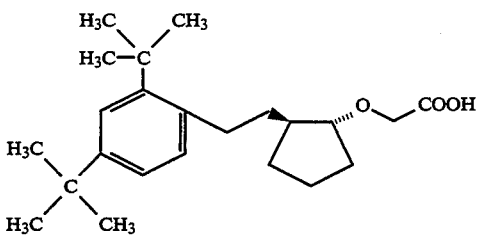

The title compound is prepared by the method of Example 15 except that the title trans isomer of Example 14 is used in place of the title cis isomer of Example 14.

EXAMPLE 17

3,5-bis(1,1-dimethylethyl)benzeneacetonitrile (17)

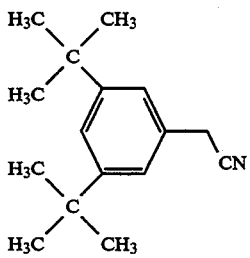

A solution of 2.00 g (8.37 mmoles) of the title product of Example 3 and 3.36 g (12.6 mmoles) of tetra-n-butylammonium cyanide in 40 ml of dichloromethane is stirred at reflux. After disappearance of starting material as judged by thin layer chromatography (TLC), the mixture is directly chromatographed using mixtures of ethyl acetate and hexane as eluents to give the title compound.

EXAMPLE 18

3,5-bis(1,1-dimethylethyl)benzeneacetaldehyde (18)

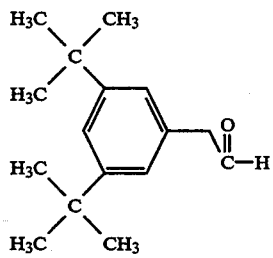

To 5.2 ml of a stirred, cold (−78°) 1.0M solution of diisobutylaluminum hydride in toluene under a nitrogen atmosphere is added dropwise a solution of 1.00 g (4.37 mmoles) of the title product of Example 17 in 15 ml of toluene. After stirring for one hour, the mixture is quenched with addition of methanol, and warmed to room temperature. Aqueous sulfuric acid (2M) is then added and the two phase mixture stirred rapidly for one hour. The layers are separated, the organic layer evaporated, and the residue chromatographed over silica gel using mixtures of ethyl acetate and hexane as eluents to give the title compound.

EXAMPLE 19

3,5-bis (1,1-dimethylethyl) benzeneethanol (19)

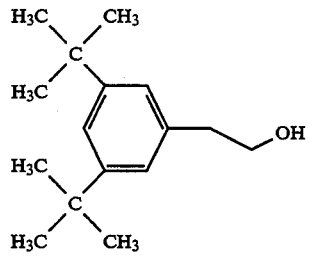

To a solution of the title product of Example 18 (500 mg, 2.14 mmoles) in ethanol (10 ml) is added a solution of sodium borohydride (80.8 mg, 2.14 mmoles) in water (1 ml). After disappearance of starting material as judged by TLC, excess reagent is destroyed by addition of acetic acid, and the mixture concentrated. The residue is partitioned between diethyl ether and water, the organic layer dried over sodium sulfate, filtered, and evaporated. Chromatography of the residue over silica gel using mixtures of ethyl acetate and hexane as eluents affords the title compound.

EXAMPLE 20

1,3-bis (1,1-dimethylethyl) -5-(2-chloroethyl)benzene (20)

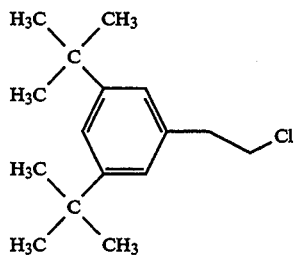

The title compound is prepared by the method of Example 11 except that the title product of Example 19 is used in place of the title product of Example 10.

EXAMPLE 21 methyl 1-[2-[3,5-bis(1,1-dimethylethyl)phenyl]-ethyl]-2-oxocyclopentanecarboxylate (21)

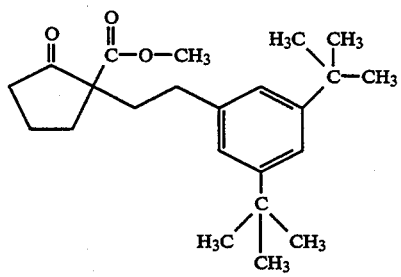

The title compound is prepared by the method of Example 12, except that the title product of Example 20 is used in place of the title product of Example 11.

EXAMPLE 22

2-[2-[3,5-bis(1,1-dimethylethyl)phenyl]-ethyl]cyclopentanone (22)

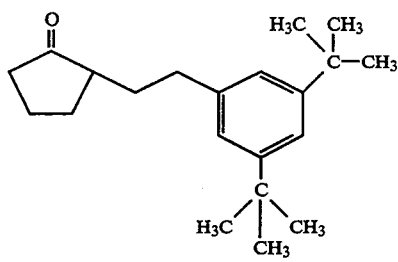

The title compound is prepared by the method of Example 13, except that the title product of Example 21 is used in place of the title product of Example 12.

EXAMPLE 23

(cis)-2-[2-[3,5-bis(1,1-dimethylethyl)-phenyl]ethyl]cyclopentanol (23, Compound A) and (trans) -2-[2-[3,5-bis(1,1-dimethylethyl)-phenyl]ethyl]cyclopentanol (23, Compound B)

Compound A

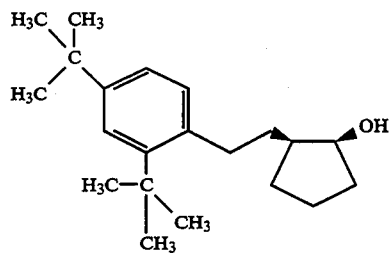

Compound B

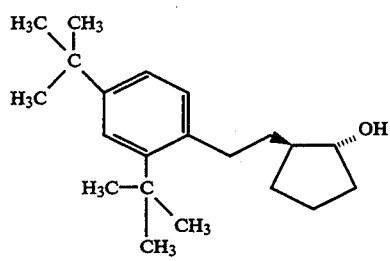

The title compounds are prepared by the method of Example 14, except that the title product of Example 22 is used in place of the title product of Example 13.

EXAMPLE 24

(cis) -2-[2-[2-[3,5-bis(1,1-dimethylethyl)-phenyl]ethyl]cyclopentyl]oxy]acetic acid (24)

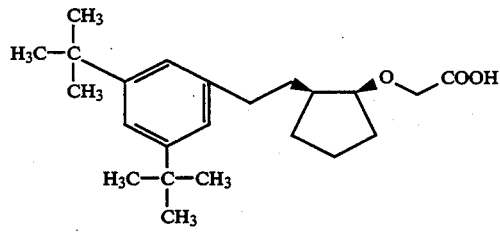

The title compound is prepared by the method of Example 15, except that the title cis isomer of Example 23 is used in place of the title cis isomer of Example 14.

EXAMPLE 25

(trans) -2-[[2-[3,5-bis(1,1-dimethylethyl)-phenyl]ethyl]cyclopentyl]oxy]acetic acid (25)

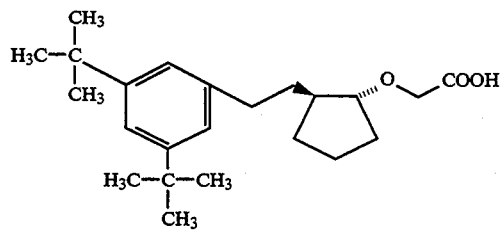

The title compound is prepared by the method of Example 15, except that the title trans isomer of Example 23 is used in place of the title trans isomer of Example 14.

EXAMPLE 26

2,4-bis(1,1,-dimethylethyl)benzenemethanol (26)

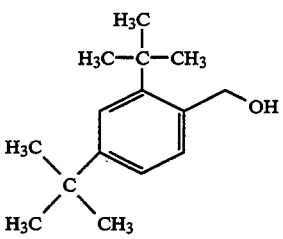

To 243 mg (10 mmoles) of magnesium turnings in 10 ml of tetrahydrofuran is added dropwise a solution of 2.69 grams (10 mmoles) of the title product of Example 9 in 5 ml of tetrahydrofuran. After the addition is complete, the mixture is refluxed for one hour. Paraformaldehyde (1.0 g, excess) is then added, and refluxing continued for one hour. The mixture is cooled to room temperature and partitioned between saturated ammonium chloride and diethyl ether. The aqueous layer is further extracted with ether, the combined organic extracts washed with brine, dried over sodium sulfate, filtered, and evaporated. Chromatography of the residue over silica gel using mixtures of ethyl acetate and hexane as eluents gives the title compound.

EXAMPLE 27

2,4-bis (1,1-dimethylethyl)-1-chloromethylbenzene (27)

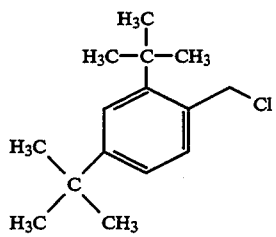

The title compound is prepared by the method of Example 11, except that the title product of Example 26 is used in place of the title compound of Example 10.

EXAMPLE 28 methyl 1-[[2,4-bis(1,1-dimethylethyl)phenyl]-methyl]-2-oxocyclopentanecarboxylate (28)

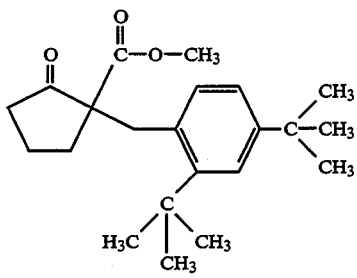

The title compound is prepared by the method of Example 12, except that the title product of Example 27 is used in place of the title product of Example 11.

EXAMPLE 29

2[[2,4-bis(1,1-dimethylethyl)phenyl]-methyl]cyclopentanone (29)

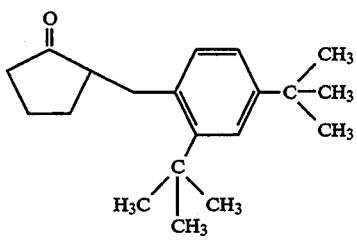

The title compound is prepared by the method of Example 13, except that the title product of Example 28 is used in place of the title product of Example 12.

EXAMPLE 30

(cis) -2-[[2,4-bis(1,1-dimethylethyl)phenyl]-methyl]cyclopentanol (30, Compound A) and (trans) -2-[[2,4-bis(1,1-dimethylethyl)phenyl]-methyl]cyclopentanol (30, Compound B)

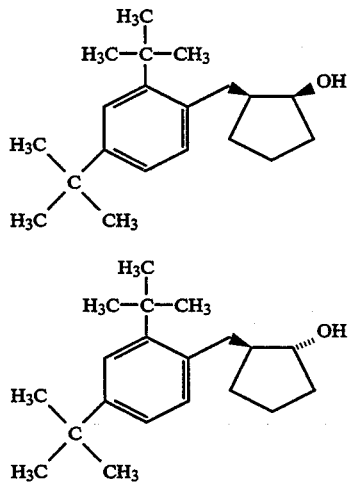

The title compounds are prepared by the method of Example 14, except that the title product of Example 29 is used in place of the title product of Example 13.

EXAMPLE 31

(cis)-2-[[2-[[2,4-bis(1,1-dimethylethyl)phenyl]-methyl]-cyclopentyl]oxy]acetic acid (31)

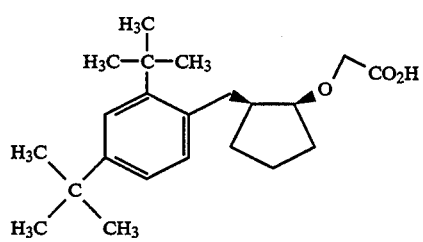

The title compound is prepared by the method of Example 15, except that the title cis isomer of Example 20 is used in place of the title cis isomer of Example 14.

EXAMPLE 32

(trans) -2-[[2-[[2,4-bis(1,1-dimethylethyl)phenyl]-methyl]cyclopentyl]oxy acetic acid (32)

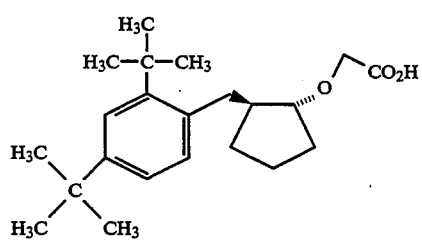

The title compound is prepared by the method of Example 16, except that the title trans isomer of Example 30 is used in place of the title trans isomer of Example 14.

EXAMPLE 33 methyl 1-[[3,5-bis(1,1-dimethylethyl)phenyl]-methyl]-2-oxocyclohexanecarboxylate (33)

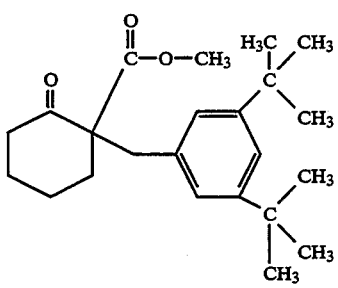

The title compound is prepared by the method of Example 12, except that 2-carbomethoxycyclohexanone is used in place of 2-carbomethoxycyclopentanone, and that the title product of Example 3 is used in place of the title product of Example 11.

EXAMPLE 34

2-[[3,5-bis(1,1-dimethylethyl)phenyl]-methyl]cyclohexanone (34)

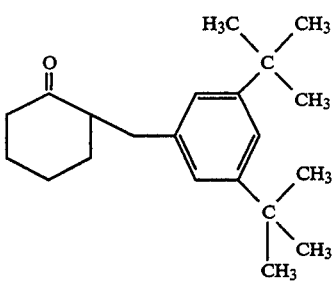

The title compound is prepared by the method of Example 13, except that the title product of Example 33 is used in place of the title product of Example 12.

EXAMPLE 35

(cis)-2-[[3,5-bis(1,1-dimethylethtl]phenyl]-methyl]cyclohexanol (35, Compound A) and (trans)-2-[[3,5-bis(1,1-dimethylethyl)phenyl]-methyl]cyclohexanol (35, Compound B)

Compound A

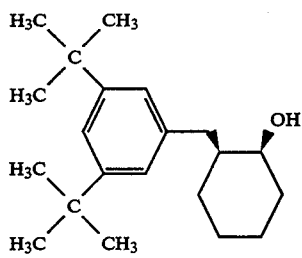

Compound B

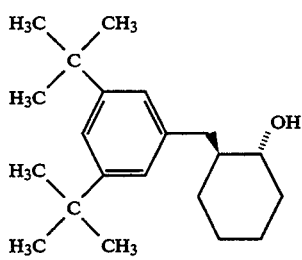

The title compounds are prepared by the method of Example 14, except that the title product of Example 34 is used in place of the title product of Example 13.

EXAMPLE 36

(cis)-2-[[2[[3,5-bis(1,1-dimethylethyl)phenyl]-methyl]-cyclohexyl]oxy]acetic acid (36)

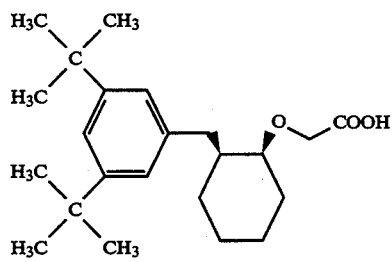

The title compound is prepared by the method of Example 15, except that the title cis isomer of Example 35 is used in place of the title cis isomer of Example 14.

EXAMPLE 37

(trans)-2-[[2-[[3,5-bis(1,1-dimethylethyl)phenyl]-methyl]cyclohexyl]oxy]acetic acid (37)

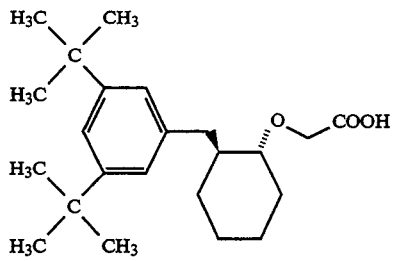

The title compound is prepared by the method of Example 16, except that the title trans isomer of Example 35 is used in place of the title trans isomer of Example 14.

EXAMPLE 38

(cis)-2-[2-[3,5-bis(1,1-dimethylethyl)phenyl]-ethyl]cyclopentyl-4-methylbenzenesulfonate (38 )

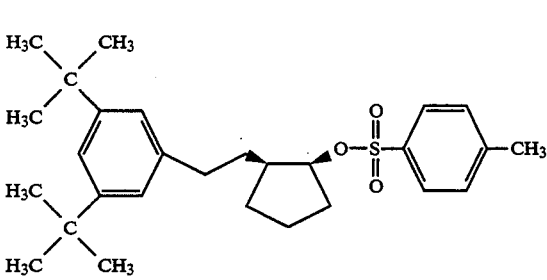

To a solution of 500 mg (1.65 mmoles) of the title cis isomer of Example 23 in 20 ml of dichloromethane is added 333 mg (3.30 mmoles) of triethylamine, and then 630 mg (3.30 mmoles) of p-toluenesulfonyl chloride. After the disappearance of starting material as determined by TLC, the mixture is washed with dilute aqueous hydrochloric acid and then water, dried over sodium sulfate, filtered, and evaporated. Chromatography of the residue over silica gel using mixtures of ethyl acetate and hexane as eluent gives the title compound.

EXAMPLE 39 methyl(trans)-2-[[2-[2-[3,5-bis(1,1-dimethylethyl) -phenyl]ethyl]cyclopentyl]thio]acetate (39)

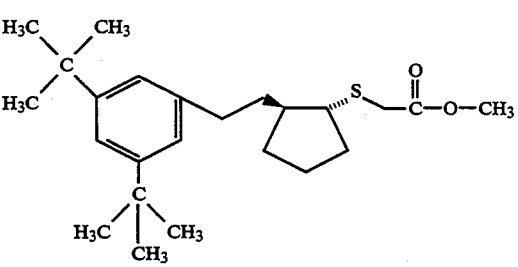

To a solution of sodium methoxide (prepared from 38 mg of sodium) in 10 ml of methanol is added 174 mg (1.64 mmoles) of methyl thioglycolate. After stirring for a few minutes, a solution of 500 mg (1.09 mmoles) of the title product of Example 38 in 5 ml of methanol is added, and stirring is continued until TLC indicates the reaction is complete. The mixture is then partitioned between diethyl ether and water, the organic layer dried over sodium sulfate, filtered, and evaporated. Chromatography of the residue over silica gel using mixtures of ethyl acetate and hexane as eluents gives the title compound.

EXAMPLE 40

(trans)-2-[[2-[2-[3,5-bis(1,1-dimethylethyl)-phenyl]ethyl]cyclopentyl]thio]acetic acid (40)

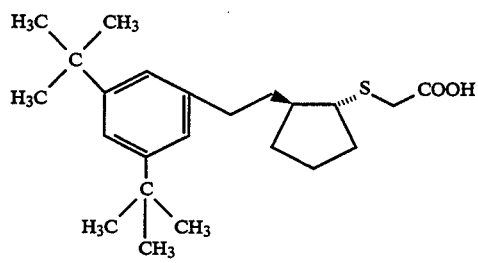

To a solution of 300 mg (0,767 mmole) of the title product of Example 39 in 5 ml methanol is added 5 ml of 1M aqueous sodium hydroxide. After stirring at room temperature, the mixture is acidified with dilute aqueous hydrochloric acid and extracted with diethyl ether. The organic layer is dried over sodium sulfate, filtered, and evaporated. Chromatography of the residue over silica gel using mixtures of ethyl acetate, hexane, and acetic acid as eluents gives the title compound.

EXAMPLE 41

(cis)-2-[[3,5-bis(1,1-dimethylethyl)phenyl]-methyl]cyclopentyl-4 -methylbenzenesulfonate (41)

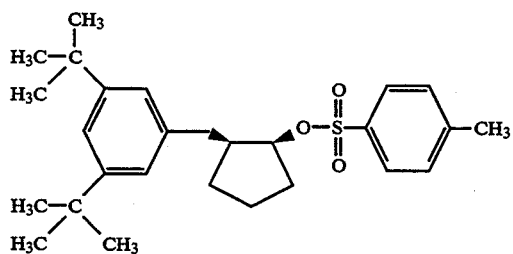

The title compound is prepared by the method of Example 38, except that the title cis isomer of Example 30 is used in place of the title cis isomer of Example 23.

EXAMPLE 42 methyl(trans)-2-[[2-[[3,5-bis(1,1-dimethylethyl) -phenyl]methyl]cyclopentyl]thio]acetate (42)

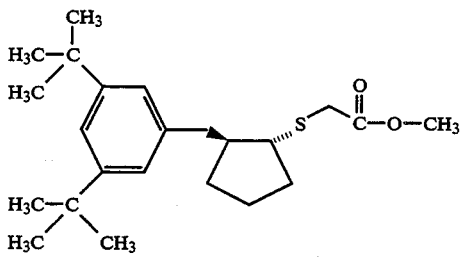

The title compound is prepared by the method of Example 39, except that the title product of Example 41 is used in place of the title product of Example 38.

EXAMPLE 43

(trans)-2-[[2-[3,5-bis(1,1-dimethylethyl)-phenyl]methyl]cyclopentyl]thio]acetic acid (43)

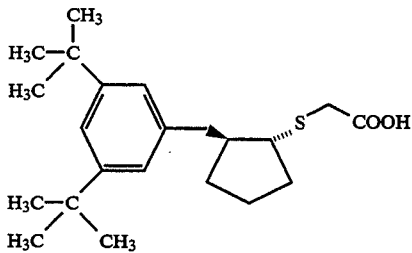

The title compound is prepared by the method of Example 40, except that the title product of Example 42 is used in place of the title product of Example 39.

EXAMPLE 44

3,6-dioxabicyclo[3.1.0]hexane (44)

To a stirred mixture of 13.1 g (188 mmoles) of 2,5-dihydrofuran and 450 ml of dichloromethane was added 38.2 g (221 mmoles) of m-chloroperoxybenzoic acid. After stirring for 20 hours, the mixture was filtered and the separated solid washed with dichloromethane. The filtrate was washed with saturated aqueous sodium bicarbonate containing $Na_2S_2O_3$ and then saturated aqueous sodium carbonate, and dried over sodium sulfate. The mixture was filtered and evaporated. Distillation of the residue first at atmospheric pressure and then under vacuum gave 6.7 g of the title compound as a liquid, b.p. 40–45° C. (15 mm). The structure was supported by $^1$H NMR.

EXAMPLE 45

(trans)-4-[[3,5-bis(1,1-dimethylethyl)-phenyl]methyl]furan-3-ol (45)

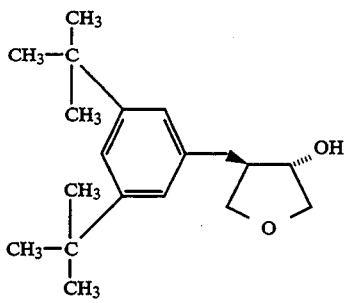

The title compound is prepared by the method of Example 10, except that the title product of Example 44 is used in place of ethylene oxide.

EXAMPLE 46

(trans)-2-[[4-[[3,5-bis(1,1-dimethylethyl)-phenyl]methyl]furan-3-yl]oxy]acetic acid (46)

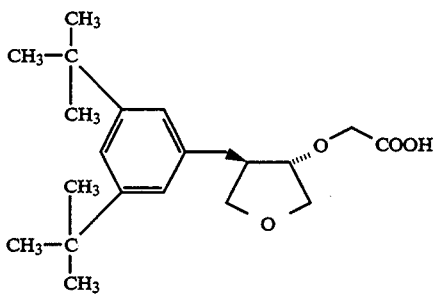

The title compound is prepared by the method of Example 15, except that the title product of Example 45 is used in place of the title cis isomer of Example 14.

EXAMPLE 47

(cis)-2[[3,5-bis(1,1-dimethylethyl)phenyl]methyl]-cyclopentanol (47, Enantiomeric Alcohol A) and methyl (cis)-2-[2-[[3,5-bis(1,1-dimethylethyl)-phenyl]methyl]cyclopentyl]acetate (47, Acetate)

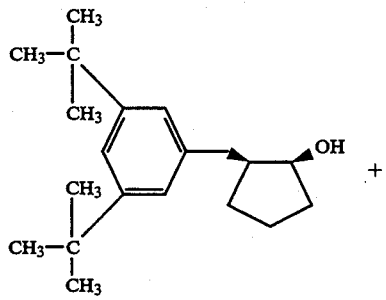

Enantiomeric Alcohol A

+

-continued

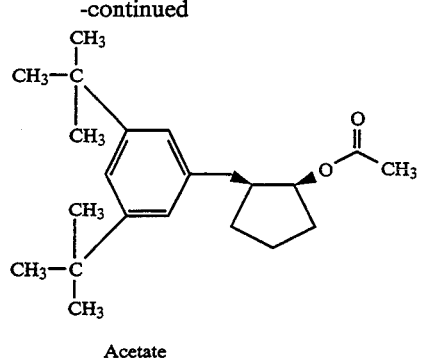

Acetate

A mixture of the title racemic cis alcohol (1.00 g, 3.47 mmoles) of Example 6 (Compound A) and AMANO Lipase PS30 (1.00 g) in 20 ml of vinyl acetate is stirred at room temperature for 24 hours. The mixture is filtered and evaporated. Chromatography of the residue over silica gel using mixtures of ethyl acetate and hexane as eluents gives enantiomerically pure title alcohol (Enantiomeric Alcohol A) and enantiomerically pure title acetate (Acetate).

EXAMPLE 48

(cis)-2-[[3,5-bis(1,1-dimethylethyl)phenyl]-methyl]cyclopentanol (48)

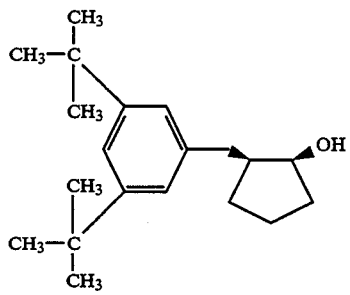

A mixture of the title enantiomerically pure acetate of Example 47 (400 mg, 1.21 mmoles), 10 ml of methanol, and 10 ml of 1N aqueous sodium hydroxide is stirred at room temperature. When thin layer chromatographic analysis indicates consumption of starting material, the mixture is partitioned between diethyl ether and water. The aqueous layer is further extracted with ether and the combined organic extracts are washed with brine and dried over sodium sulfate. The drying agent is filtered and evaporated. Chromatography of the residue over silica gel using mixtures of ethyl acetate and hexane as eluents gives enantiomeric alcohol B, the enantiomerically pure title alcohol with opposing rotation as compared to the enantiomeric alcohol A from Example 47.

The enantiomerically pure alcohols from Examples 47 and 48 above may be converted to the enantiomerically pure carboxylic acids shown below according to the procedure described in Example 7:

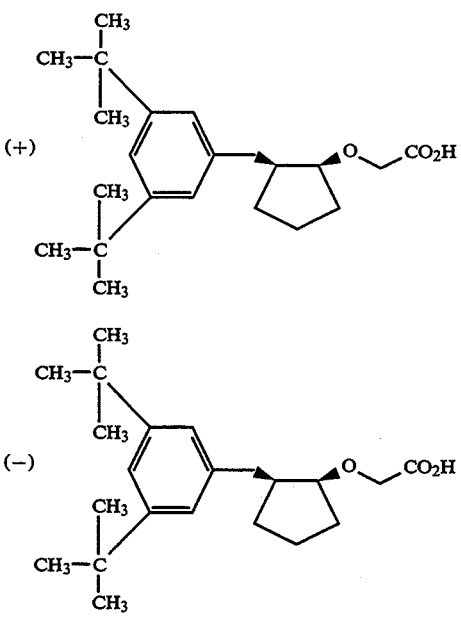

The foregoing examples are provided to enable one of ordinary skill in the art to practice the present invention. These examples are merely illustrative, however, and should not be read as limiting the scope of the invention as it is claimed in the appended claims.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound of the formula:

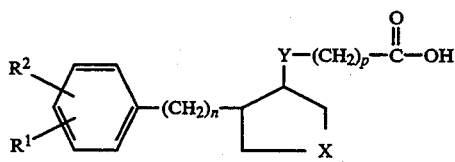

Formula I or a pharmaceutically acceptable salt thereof, wherein:
$R^1$ and $R^2$ are each alkyl;
n is an integer of from 1 to 4;
x is oxygen or $-(CH_2)_m-$;
m is an integer of from 1 to 3;
y is oxygen or sulfur; and
p is an integer of from 1 to 4.

2. A compound of claim 1 wherein Y is oxygen.
3. A compound of claim 2 wherein X is $-(CH_2)_m-$.
4. A compound of claim 3 wherein $R^1$ and $R^2$ are each tert-butyl.
5. A compound of claim 4 wherein n is 1.
6. A compound of claim 5 wherein p is 1.
7. A compound of claim 6 wherein m is 1.
8. A compound of claim 1 having the structure:

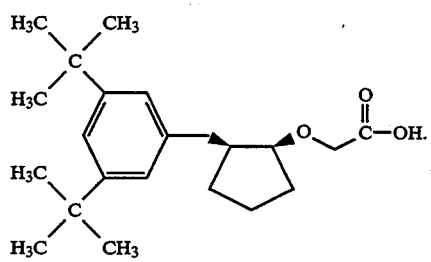

9. A compound of claim 1 having the structure:

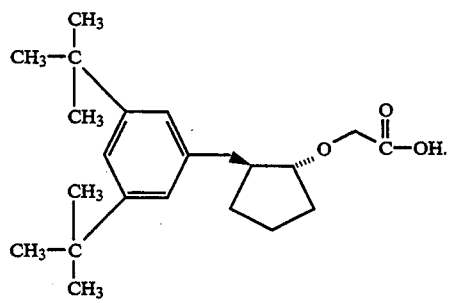

10. A pharmaceutical composition comprising a pharmaceutically-acceptable carrier and a pharmaceutically-effective amount of a compound of the formula:

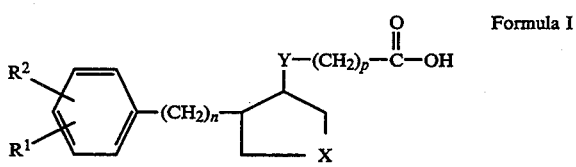

Formula I or a pharmaceutically acceptable salt thereof, wherein:
$R^1$ and $R^2$ are each alkyl;
n is an integer of from 1 to 4;
X is oxygen or $-(CH_2)_m-$;
m is an integer of from 1 to 3;
Y is oxygen or sulfur; and
p is an integer of from 1 to 4.

11. The pharmaceutical composition of claim 10 wherein the compound is (cis)-2-[[2-[3,5-bis(1,1-dimethylethyl)phenylmethyl]cyclopentyl]oxy]acetic acid (7) or (trans)-2-[[2-[3,5-bis(1,1-dimethylethyl)-phenylmethyl]cyclopentyl]oxy]acetic acid (8).

12. A method of treating an inflammation-associated disorder in an animal in need of such treatment comprising administering to the animal a therapeutically-effective amount of a compound of the formula:

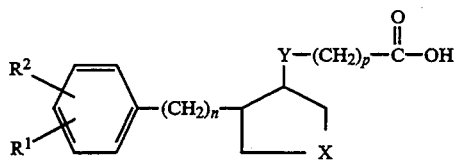

Formula I or a pharmaceutically acceptable salt thereof, wherein:
$R^1$ and $R^2$ are each alkyl;
n is an integer of from 1 to 4;
X is oxygen or $-(CH_2)_m-$;
m is an integer of from 1 to 3;
Y is oxygen or sulfur; and
p is an integer of from 1 to 4.

13. The method of claim 12 wherein the compound is (cis)-2-[[2-[3,5-bis(1,1-dimethylethyl)-phenylmethyl]cyclopentyl]oxy]acetic acid (7) or (trans)-2-[[2-[3,5-bis(1,1-dimethylethyl)-phenylmethyl]cyclopentyl]oxy]acetic acid (8).

* * * * *

UNITED STATES PATENT AND TRADEMARK OFFICE
CERTIFICATE OF CORRECTION

PATENT NO. : 5,420,343
DATED : May 30, 1995
INVENTOR(S) : Mueller, et al.

It is certified that error appears in the above-indentified patent and that said Letters Patent is hereby corrected as shown below:

Column 4, line 61, reading "-4hydroxystyrenes" should read ---4-hydroxystyrenes--.

Column 6, line 44, reading "(977)" should read --(1977)--.

Column 7, line 22, reading "-butyl" should read --t-butyl--.

Column 12, line 55, reading "Compounds 7" should read --Compounds 6--.

Column 15, line 58, reading "(a) preparation" should read -- (a) Preparation--.

Column 18, line 15, reading "ICsO" should read --$IC_{50}$--.

Column 23, line 36, reading"Example 7" should read --Example 6--.

Column 27, line 4, reading "Oxy" should read --oxy--.

Column 32, line 22, reading "20" should read --30--.

Column 35, line 34, reading "(0,767 mmole)" should read --(0.767 mmole)--.

Signed and Sealed this

Tenth Day of June, 1997

Attest:

BRUCE LEHMAN

*Attesting Officer*       *Commissioner of Patents and Trademarks*